United States Patent [19]

Kirschbaum

[11] Patent Number: 5,790,235

[45] Date of Patent: Aug. 4, 1998

[54] METHOD AND APPARATUS TO MEASURE PUPIL SIZE AND POSITION

[75] Inventor: Alan R. Kirschbaum, Oakland, Calif.

[73] Assignee: Carl Zeiss, Inc., Thornwood, N.Y.

[21] Appl. No.: 827,380

[22] Filed: Mar. 26, 1997

[51] Int. Cl.$^6$ .............................. A61B 3/00; A61B 3/14
[52] U.S. Cl. ...................... 351/246; 351/206; 351/210
[58] Field of Search .................................. 351/200, 204, 351/206, 210, 246, 205; 382/62, 63

[56] References Cited

U.S. PATENT DOCUMENTS

| | | | |
|---|---|---|---|
| 4,836,670 | 6/1989 | Hutchinson | 351/210 |
| 4,950,069 | 8/1990 | Hutchinson | 351/210 |
| 4,973,149 | 11/1990 | Hutchinson | 351/210 |
| 5,036,347 | 7/1991 | Tsunekawa et al. | 354/400 |
| 5,214,455 | 5/1993 | Penney et al. | 351/210 |
| 5,220,361 | 6/1993 | Lehmer et al. | 351/226 |
| 5,231,674 | 7/1993 | Cleveland et al. | 382/6 |
| 5,416,317 | 5/1995 | Nishimura et al. | 250/221 |
| 5,481,622 | 1/1996 | Gerhardt et al. | 382/103 |
| 5,491,757 | 2/1996 | Lehmer et al. | 382/128 |

OTHER PUBLICATIONS

"Eye Movement Analysis System Using Fundus Images" by H. Kawai, S. Tamura, K. Kani, and K. Kariya, *Pattern Recognition*, vol. 19, No. 1, pp. 77–84, 1986.

"Methods and Designs, Survey of eye movement recording methods" by L.R. Young and D. Sheena, *Behavior Research Methods & Instrumentation*, vol. 7(5), pp. 397–429, 1975.

*Primary Examiner*—Huy Mai
*Attorney, Agent, or Firm*—Michael B. Einschlag

[57] ABSTRACT

Embodiments of the present invention are method and apparatus for measuring the size and position of an eye's pupil, and for doing so rapidly. In particular, embodiments of the present invention are methods and apparatus for determining pupil size and position without measuring the full pupil and for doing so rapidly, in real time, as data are being collected. An embodiment of the present invention is a method for determining a size of an eye's pupil which comprises the steps of: (a) storing reference partial areas for a reference pupil that are associated with scan lines of a two-dimensional image of the eye; (b) analyzing one or more scan lines comprised of pixels from another two-dimensional image of the eye as follows: (c) determining of which the pixels in an analyzed scan line are in the pupil; (d) determining a sum of such pixels for the analyzed scan line; (e) determining a partial area corresponding to the scan line by adding the sum to the partial area for previously analyzed scan lines; and (f) estimating the size of the pupil from the partial areas determined from the another two dimensional image and the partial areas for the reference pupil. Further, the inventive and apparatus utilizes an iterative estimation procedure that may be terminated whenever successive estimates satisfy a predetermined convergence criterion.

10 Claims, 5 Drawing Sheets

METHOD AND APPARATUS TO MEASURE PUPIL SIZE AND POSITION

TECHNICAL FIELD OF THE INVENTION

The present invention relates to method and apparatus for measuring geometric properties and position of an eye's pupil and, in particular, for measuring the size and position of the pupil.

BACKGROUND OF THE INVENTION

Measurement of geometric properties and position of an eye's pupil, and changes thereto, can provide important information in physiological testing and medical diagnosis. One example of the use of measurements of geometric properties of the pupil relates to a phenomenon wherein the pupil undergoes an involuntary contraction and recovery whenever the eye is exposed to a stimulus such as a brief flash of light. This recovery has a characteristic time signature and amplitude (referred to as the pupillary response) that are related to the brightness of the stimulus. As such, the amplitude of the pupillary response (related to pupil size) and the velocity of the pupillary response (related to changes in pupil size) can be used to map the sensitivity of the eye's visual field. As one can readily appreciate, to do this requires method and apparatus for rapidly measuring pupil size.

Another example of the use of measurements of geometric properties of the pupil relates to a well known phenomenon wherein certain anesthetics cause the pupil to become dilated. Here, measurements of pupil size can be used as a measure of the depth of anesthesia.

Still another example of the use of measurements of geometric properties of the pupil relates to medical diagnostic applications that require continuous measurement of gaze direction, i.e., orientation of the visual axis of the eye. As is well known, many present methods of measuring gaze direction do so by comparing the position of the center of the pupil with the position of a virtual image of a distant point source of light formed by the cornea, often referred to as the corneal reflex (the distance between the corneal reflex and the center of the pupil is linearly related to the angle of rotation of the eye). As one can readily appreciate, such applications require rapid, sequential measurements of pupil position.

There are several sets of methods known in the prior art for determining pupil size and position. For example, a first set of such prior art methods utilizes a video system to form an image of the pupil on the surface of a two-dimensional solid state detector, for example, a CCD device, or a vidicon tube. In at least some of these methods, the eye is illuminated so that, in the image, the pupil is darker than the iris and surrounding tissue. When this is done, in accordance with this first set of such prior art methods, the pupil is identified as being comprised of image pixels having a brightness less than a specified threshold. Next, the pupil size is taken as being equal to the total number of pixels associated with the pupil, and the position of the center of the pupil is taken as being equal to the center of gravity of the pixels associated with the pupil.

A second set of such prior art methods also utilizes a video system to form an image of the pupil on the surface of a two-dimensional solid state detector or a vidicon tube. Again, in at least some of these methods, the eye is illuminated so that, in the image, the pupil is darker than the iris and surrounding tissue. When this is done, in accordance with this second set of such prior art methods, the pupil size and position are determined by first finding left and right edge points of the pupil on all video scan lines that intersect the pupil. These left and right edges are found, in one example of such prior art methods, by determining zero crossings of the second derivative of a brightness distribution along each video scan line. Then, the pupil size is taken as being equal to the sum of all chord lengths for the pupil; a chord length being defined by the distance between the left and right edge points of the pupil, and the position of the center of the pupil is taken as being equal to the center of gravity of the chord lengths.

A third set of such prior art methods uses an assumption that the pupil has a simple geometric shape, typically that of a circle or an ellipse. Then, in accordance with this third set of such prior art methods, the locations of a few points on the edge of the pupil are measured and, using these points, a least squares fit is performed to identify the edge and, therefrom, the pupil size and position are determined.

A fourth set of such prior art methods uses detectors other than video detectors, for example, a four-element photodetector. Then, in accordance with this fourth set of such prior art methods, differential signals on horizontal and vertical quadrants of the photodetector are used to determine the position of the pupil center relative to the position of the center of the detector, while the sum of all four signals is used to determine the pupil size.

Each of the above-described prior art methods, except for those that use a least squares fit to an assumed pupil shape, implicitly assumes that the entire pupil is always visible. However, in practice, this is frequently not the case. Instead, in a typical case, either the upper eyelid or upper eyelashes obscure at least some part of the upper pupil. Furthermore, the amount the pupil is obscured is not the same all of the time. As a result, all of the above-described methods that depend on perceiving the entire pupil will be inaccurate since the entire pupil cannot be seen. This problem may not occur when using the least squares fitting method since only a subset of pupil edge points is required to perform the fit.

Please note, however, that even though the least squares fitting method may solve the problem caused by pupil obscuring, this method runs into a further problem. This further problem arises because the least squares fitting method assumes the pupil is circular, or elliptical or some other predetermined shape. The further problem is that a pupil seldom conforms exactly to a predetermined shape. Therefore, in using this least squares fitting method, the resulting estimate of pupil size depends on the pupil edge points selected for use in performing the least squares fit. This leads to error. Furthermore, such least squares fitting methods are computationally intensive, and may not allow for rapid measurement of pupil size changes.

In light of the above, there is a need for a method and apparatus for measuring the size and position of a pupil, and for doing so rapidly.

SUMMARY OF THE INVENTION

Advantageously, embodiments of the present invention are method and apparatus for measuring the size and position of an eye's pupil, and for doing so rapidly. In particular, embodiments of the present invention are methods and apparatus for determining pupil size and position that do not require measuring the full pupil. Further, embodiments of the inventive method and apparatus do not make a priori assumptions about the pupil shape, except that, whatever the pupil shape is, the pupil substantially maintains that shape whenever the pupil changes size. Still further, embodiments of the inventive method and apparatus require few calculations, and, therefore, advantageously enable the pupil size and position to be determined rapidly, in real time, as data are being collected.

In particular, an embodiment of the present invention is a method for determining a size of an eye's pupil which comprises the steps of: (a) storing reference partial areas for a reference pupil that are associated with scan lines of a two-dimensional image of the eye; (b) analyzing one or more scan lines comprised of pixels from another two-dimensional image of the eye as follows: (c) determining which of the pixels in an analyzed scan line are in the pupil; (d) determining a sum of such pixels for the analyzed scan line; (e) determining a partial area corresponding to the scan line by adding the sum to the partial area for previously analyzed scan lines; and (f) estimating the size of the pupil from the partial areas determined from the another two dimensional image and the partial areas for the reference pupil. Further, as will be explained in detail below, the inventive method and apparatus utilizes an iterative estimation procedure that may be terminated when successive estimates satisfy a predetermined convergence criterion.

BRIEF DESCRIPTION OF THE FIGURE

Components which are the same in the various figures have been designated by the same numerals for ease of understanding.

DETAILED DESCRIPTION

Figure 1:
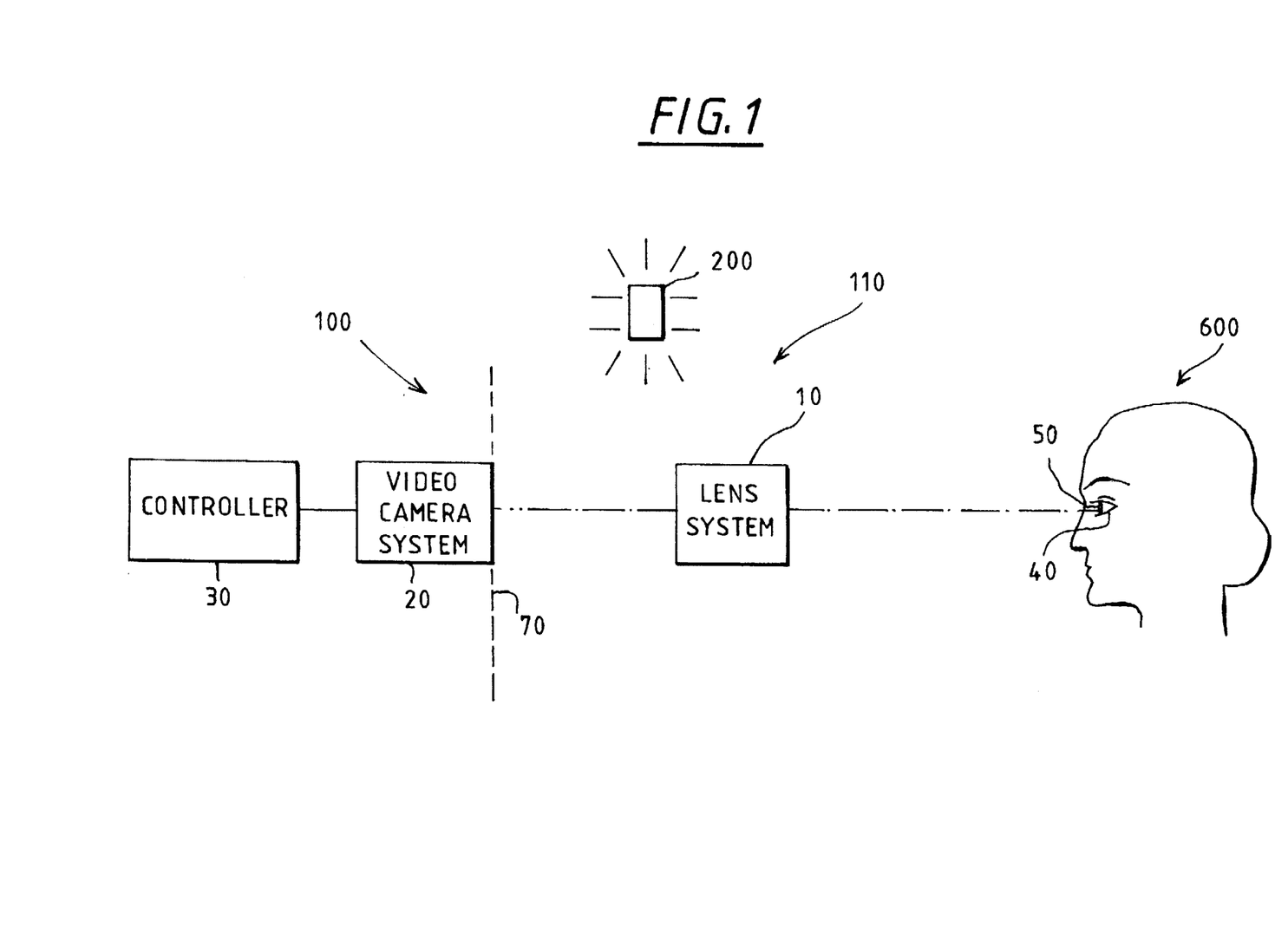
FIG. 1 shows, in pictorial form, an embodiment of the present invention.

FIG. 1 shows, in pictorial form, embodiment 100 of the present invention. As shown in FIG. 1, embodiment 100 of the present invention is comprised of eye and pupil imaging system 110 (including lens system 10 and illumination apparatus 200), video camera system 20 and controller 30 which analyzes two-dimensional ("2D") images of eye 40 (including pupil 50) of subject 600. The manner in which controller 30 analyzes the 2D images will be described in detail below.

Video camera system 20 includes, for example, a CCD video camera, and operates under the control of controller 30 in a manner which is well known by those of ordinary skill in the art to obtain 2D images of eye 40 and to transmit the 2D images to controller 30. In accordance with the present invention, the images are transmitted in the form of pixels located at the various x,y coordinates of the 2D image and having measures of brightness associated therewith. In the preferred embodiment, controller 30 is a microprocessor or a computer. In particular, the preferred embodiment of controller 30 includes a digital signal processing chip, for example, an ADSP 2105 digital processing chip made by Analog Devices, as the main calculating engine. Such a chip typically is very fast at performing simple arithmetic operations, and also typically includes a cache memory that can be used to store reference pupil data in accordance with the present invention as will be set forth in detail below.

Assume, for the sake of ease of understanding the present invention, that video camera system 20 provides 2D images in black and white. Further, although an embodiment of the invention is described wherein 2D images obtained by video camera system 20 are analyzed in real time, the method and apparatus of the present invention are not so limited. In fact, embodiments of the method and apparatus of the present invention may be used to determine the size and position of the pupil from 2D images obtained from storage media such as video tape or CD ROM or computer disk and then transmitted to controller 30. In addition, the 2D images may be obtained from photographs taken by a film camera, which photographs are then converted to a form suitable for analysis by controller 30 (for example, digital form) by many methods and apparatus that are well known to those of ordinary skill in the art such as, for example, by optical scanners.

As shown in FIG. 1, imaging system 110 is comprised of a light source 200 and a lens system 10 that images eye 40 at plane 70. As further shown in FIG. 1, video camera system 20 is located at plane 70 and, in accordance with a preferred embodiment of the present invention, video camera system 20 obtains a 2D image of eye 40 that is comprised of video scan lines. Each of the video scan lines is comprised of a predetermined number of pixels, each of which pixels has brightness information associated therewith. In a preferred embodiment of the present invention, the 2D video images are produced by video scans that start from the bottom of pupil 50 and go up to the top of pupil 50. Alternatively, video camera system 20 can scan from the top to the bottom of pupil 50. However, the same effect as that of doing a video scan from bottom-to-top can be achieved by: (a) inverting the 2D image of the top-to-bottom scan in accordance with methods which are well known to those of ordinary skill in the art or (b) changing (for example, inverting) the order in which received pixel data that comprises the 2D image from a top-to-bottom scan is stored, or referred to, by controller 30 or video camera system 20 in accordance with methods that are well known to those of ordinary skill in the art. As will be explained in detail below, in accordance with this embodiment of the present invention, data processing of the pixels comprising the 2D image begins with pixels obtained from the bottom of the pupil image. Note that for the embodiment described below, for a top-to-bottom scan (unlike a bottom-to-top scan where calculations may begin as soon as data from each scan line is received), the scan data must be stored, and calculations do not begin until data from a full video frame has been acquired.

Video camera system 20 may include a CCD camera which directly outputs digital data or, as is well known in the art, video camera system 20 may comprise a video camera whose output images are digitized by a frame grabber or video imaging board whose output is applied as input to controller 30. Such apparatus are well known to those of ordinary skill in the art. Further, it is preferred that light source 200 output infrared radiation which is not detected by, and is sufficiently low intensity that it will not injure, a patient. Still further, it well known in the art that light source 200 may be mounted substantially coaxial with lens system 10 to provide a bright pupil in the video image due to backscattered light from the retina or that light source 200 may be mounted sufficiently displaced from lens system 10 to provide a dark pupil in the video image. Yet still further, infrared sensitive video cameras are well known in the art.

The following describes the analysis of the 2D images to provide the size and position of the pupil in accordance with the present invention. However, before discussing the detailed embodiments of the inventive method and apparatus, a discussion is presented of the inventor's discovery that enables embodiments of the present invention to measure the size and position of the pupil, and to do so even when the pupil is partly obscured.

Figure 2:
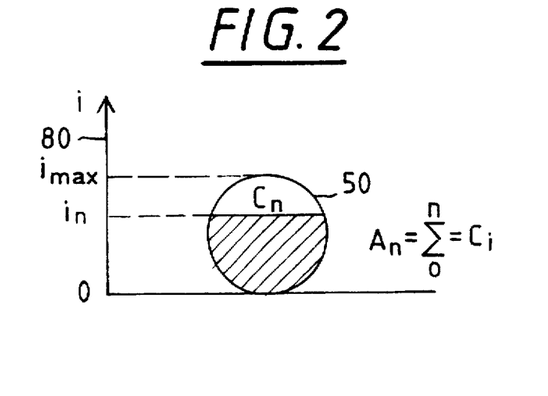
FIG. 2 shows, in pictorial form, a coordinate system and a partial area $A_n$ used in accordance with the present invention.

In order to understand the inventor's discovery, one refers to FIG. 2 which shows, in pictorial form, a coordinate system and a partial area $A_n$ used in accordance with the present invention. As shown in FIG. 2, the origin of vertical axis 80 of the coordinate system is placed at the lower edge of pupil 50 and vertical axis 80 is directed toward the top of pupil 50. An index i is used in accordance with the present invention to denote a horizontal video scan line. Referring to FIG. 2, each horizontal video scan line in that passes through pupil 50, produces a chord $c_n$ that is defined by left and right edges of pupil 50. In accordance with the present invention, left and right edges of pupil 50 are located for each video scan line. This may be accomplished by controller 30 in accordance with any one of a large number of methods that are well known to those of ordinary skill in the art such as, for example, by thresholding with respect to brightness levels between the pupil and surrounding areas of the eye or by zero-crossing. Suitable methods are disclosed in U.S. Pat. No. 5,491,757 and 5,220,361, both of which patents are incorporated herein by reference. However, note that, in accordance with the present invention, the specific method used to locate the left and right edges of pupil 50 is not critical. Further, the lower edge of pupil 50 may be determined in accordance with a large number of methods that are well known to those of ordinary skill in the art, for example, it may be simply taken as the first detected chord of the pupil.

As indicated in FIG. 2, a portion of pupil 50 below and including chord $c_n$ (shown as the shaded portion) is designated by index in and has an area An called a partial area. The partial area is defined as being equal to the sum of all the chord lengths below and including the horizontal video scan line denoted by index in. In particular, partial area $A_n$ is defined as:

$$A_n = \sum_{0}^{n} c_i \quad (1)$$

Figure 3:
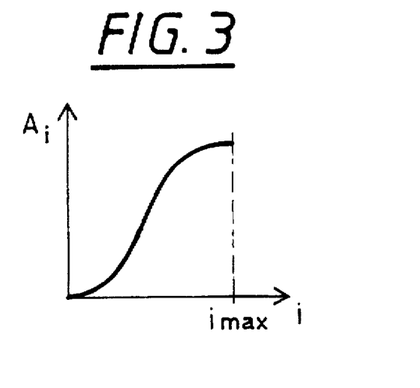
FIG. 3 shows, in graphical form, partial area $A_n$ as a function of length along a vertical axis of the coordinate system shown in FIG. 2.

FIG. 3 shows, in graphical form, partial area An as a function of length along the vertical axis of the coordinate system shown in FIG. 2 (vertical height). Hence, partial area $A_n$ is a function of horizontal video scan line position i. Further, in accordance with the inventor's discovery, the form of this function depends on the shape of pupil 50. For convenience and ease of understanding the present invention, the shape of pupil 50 is shown herein as being circular.

Figure 4:
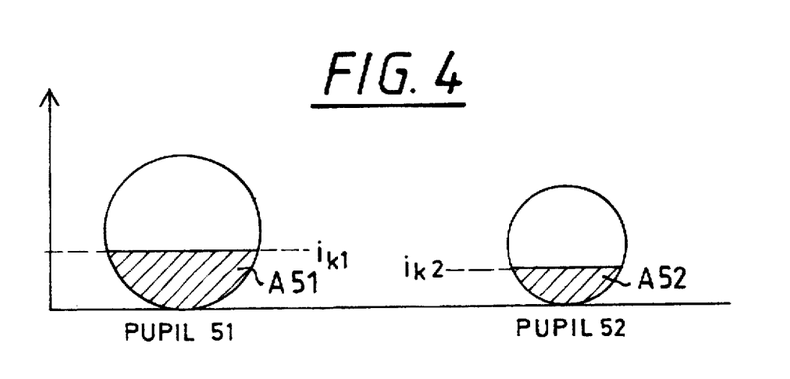
FIG. 4 shows, in pictorial form, pupils 51 and 52 that have different sizes but the same shape.

FIG. 4 shows, in pictorial form, pupils 51 and 52 that have different sizes but the same shape. The inventor has discovered that the ratio of partial areas $A_{S1}$, and $A_{S2}$ that lie below and including horizontal video scan lines $i_{k1}$, and $i_{k2}$, respectively, is the same as the ratio of the total areas of pupils 51 and 52 if horizontal video scan lines $i_{k1}$, and $i_{k2}$ cross pupils 51 and 52, respectively, at corresponding heights.

The manner is which the inventor's discovery is used to fabricate embodiments of the present invention is now described in detail below.

Assume, for purposes of understanding the present invention, that pupil 51 is a reference pupil for which a determination of partial area as a function of horizontal video scan line position has already been made. Further, in accordance with embodiments of the present invention, this function (i.e., the partial area of the reference pupil as a function of horizontal video scan line position) is stored in controller 30 or is stored and is accessible to controller 30. For example, if controller 30 is a computer, then the function can be stored in the computer memory. As is well known, the function can also be stored on storage devices such as disk, tape and the like and transferred to the computer when needed. The function can also be stored in another computer and be accessed over a link, by modem, over the internet and so forth. In practice, the reference pupil is the same pupil whose area and position are later determined in accordance with the present invention. To determine the function, the patient is asked to open his or her eye so that the entire pupil is exposed, i.e., no part of the pupil is obscured. Then, an image of the entire pupil is acquired and the partial areas are determined as a function of horizontal video scan line position. After determining this function, the size and position of the pupil are determined for use in measuring: (a) the effects of stimuli on pupil size; (b) the amplitude and velocity of a pupillary response; (c) the effects of anesthesia on pupil size (to parametrize these effects); (d) the direction of gaze; and (e) so forth.

Further assume that pupil 52 is a test pupil whose size, i.e., area, is to be determined. Then, in accordance with the present invention, for a given horizontal video scan line i across pupil 52, partial area $A_{S2}(i)$ is the accumulated sum of chord lengths for all horizontal video scan lines below and including the horizontal video scan line denoted by index i. Assume now that one knew the value of index i' of the corresponding horizontal video scan line for reference pupil 51. Then, one would retrieve the corresponding partial area $A_{S1}(i')$ from memory and the ratio of the total areas of the two pupils would be given by $R=A_{S2}(i)/A_{S1}(i')$. As one can readily appreciate from the above, i' is not known a priori. However, in accordance with the present invention, the value of i' is estimated and this estimate is used to determine an estimated value of R, the ratio of the total areas of the two pupils.

The following describes how i' and R are estimated and how these estimates are used to determine the size and location of the pupil.

The inventive method of estimating i' is iterative. For each horizontal video scan line denoted by index i, beginning at the bottom of pupil 52, one determines estimates of the value of R, denoted as R(i). Then, as the inventor has discovered, as i increases, the difference between consecutive values of R(i) decreases. This led to the discovery that if the sampling density, i.e., the number of horizontal video scan lines intersecting the pupil, were large enough, the value of R(i) would approach the true value of R well before the entire pupil was processed. Using this discovery, embodiments of the present invention terminate the iterative method whenever the absolute value of the difference between successive estimated values of R is less than a predetermined amount, i.e., whenever |R(i)−R(i+1)|<δ, where δ is a predetermined amount. Of course, the step of determining whether the present estimate is sufficiently accurate can be measured in accordance with any one of a number of methods well known to those of ordinary skill in the art.

Figure 5:
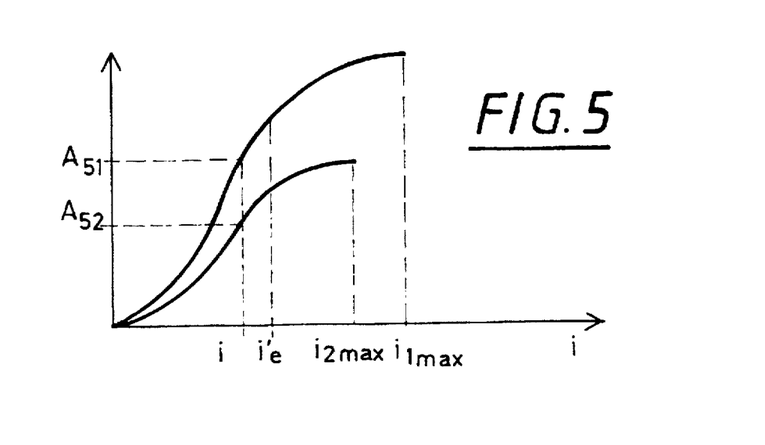
FIG. 5 shows, in graphical form, the partial areas of pupils 51 and 52 as a function of length along the vertical axis.

With the above explanation in mind, we turn to an explanation of how estimates for R are determined in accordance with a preferred embodiment of the present invention. Refer now to FIG. 5 which shows, in graphical form, the partial areas $A_{52}(i)$ and $A_{51}(i)$ of pupils 51 and 52, respectively, as a function of length along the vertical axis. Here, an estimated value of i' is denoted as $i'_e$. In accordance with the present invention, $$i'_e = i \sqrt{(1/R(i-1))} \tag{2}$$

and $$R(i) = A_{52}(i)/A_{51}(i'_e) \tag{3}$$

where $$A(i) = \sum_{n=0}^{i} c_n$$

and $c_n$=the chord length of horizontal video scan line n.

As one can readily appreciate, using the above-described preferred embodiment of the inventive method requires one to select a starting value for R, i.e., R(0). In accordance with the present invention (since the inventor has discovered that in practice R is not too far from unity), a preferred choice is R(0)=1. However, the inventor has also discovered that the results obtained using the inventive method do not depend significantly on the particular choice for R(0).

The inventor has discovered that use of the square root function in estimating $i'_e$ in accordance with eqn. (2) provides satisfactory results since ratios of corresponding linear dimensions of similar two-dimensional objects are equal to the square root of the ratio of the areas. However, embodiments of the present invention are not limited to the use of the square root function in performing the estimation. In fact, since the computation involved in determining a square root is a time-consuming operation for processors, in accordance with a preferred embodiment of the present invention, it is preferred to use either a lookup table to perform the computation of eqn. (2) or to utilize a first-order series approximation of the square root function instead.

Figure 6:
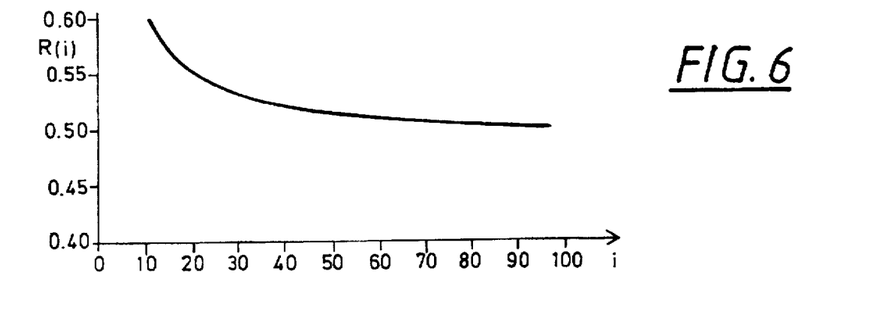
FIGS. 6 and 7 show, in graphical form, how the inventive estimation method converges when using two circular pupils having a full area ratio of 0.5, the results shown in FIGS. 6 and 7 differ only because of the number of horizontal video scan lines used to span the pupil in each case.
Figure 7:
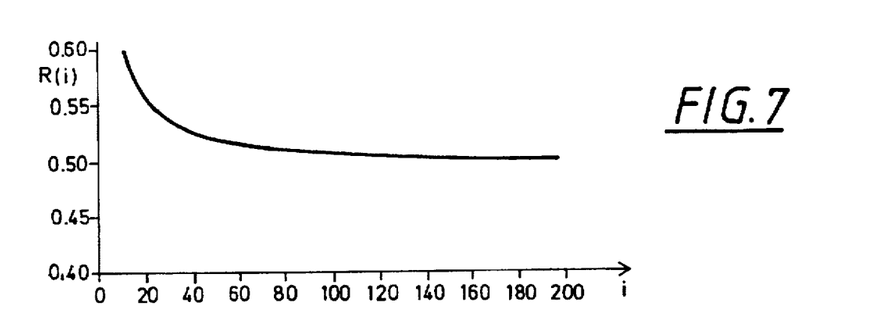

FIGS. 6 and 7 show, in graphical form, how quickly the inventive estimation method converges when using two circular pupils having a full area ratio of 0.500. The curves shown in FIGS. 6 and 7 were computed using the estimation method defined by eqns. (2) and (3) and the curves differ only because of the number of horizontal video scan lines used to span the pupil in each case. Results similar to those shown in FIGS. 6 and 7 were also obtained when using a square pupil and those results confirmed that the results of the inventive method do not depend on pupil shape. In particular, FIG. 6 shows that using 100 horizontal video scan lines gives an estimated value of the area ratio R of 0.515 at half the pupil diameter, i.e., at horizontal video scan line 50. Whereas FIG. 7 shows that using 200 horizontal video scan lines gives an estimated value of the area ratio R of 0.507 at half the pupil diameter, i.e., at horizontal video scan line 100. Please note that these values are illustrative only, and do not represent upper limits on the accuracy of the inventive method. Nevertheless, FIGS. 6 and 7 do illustrate that a specified degree of accuracy depends on image size on the video sensor.

In a further aspect of the above-described embodiment, the curves shown in FIGS. 6 and 7 are encoded, numerically or by functional approximation. Then, these representations of the curves are used to predict the asymptotic value of the estimation method, which asymptotic value is the true value of R. This is done by (a) determining the estimate of R, i.e., R(i), after analyzing the data (pixels) from a predetermined number of horizontal scan lines and (b) using the representations of the curves to determine the fraction of the true value of R for that estimate by reference to the representations of the curves as a function of horizontal scan line index i. This is described below in conjunction with eqns. (5) and (6).

For convenience, and in accordance with one aspect of the preferred embodiment of the present invention, one may choose to end the iteration of eqns. (2) and (3) at a value of i that corresponds to half the vertical pupil height of the reference pupil since, as was shown above, at this value of i, R(i) is quite close to the true value R. In this case, the iteration process is terminated whenever $i'_e > N/2$.

A second, preferred embodiment of the present invention takes advantage of the inventor's discovery that the curves shown in FIGS. 6 and 7 are universal in nature, i.e., they do not depend significantly on the shape of the pupil. This discovery is supported by modeling studies. Thus, in accordance with the present invention, the curves are a function only of (a) N, the number of sampling horizontal video scan lines spanning the reference pupil and (b) R, the true full area ratio. Using this discovery, curves are calculated for various values of N and R and a difference, δ(i), between the true value of R and estimated values of R, i.e., R(i), at various values of i is determined by using the following equation.

$$\delta(i) = R - R(i) = (R-1) * F_R(i,N) \tag{4}$$

$F_R(i, N)$ is determined by fitting the curves for various values of N and R to the form of eqn. (4) in accordance with methods that are well known to those of ordinary skill in the art. Then, $F_R(i,N)$ is stored, for example, in controller 30 or is made available to controller 30, either as a set of tabulated values for various values of R, N and i or as a set of parameters that can be used to calculate the function explicitly. If i is large enough, for example, if i has a value corresponding to half the pupil height, then R(i) is quite close to the true value R. Finally, in accordance with the present invention, δ(i) is estimated using the following equation.

$$\delta_{est}(i) = (R(i)-1) * F_{R(i)}(i,N) \tag{5}$$

Thus, after the iteration is terminated (for example, the iteration may utilize eqns. (2) and (3) and may terminate whenever $i'_e > N/2$), the estimated correction $\delta_{est}(i)$ is used to provide a corrected value of the estimate R(i) in accordance with the following equation.

$$R_{corr} = R(i) - \delta_{est}(i) \tag{6}$$

Since the calculations shown in eqns. (5) and (6) are carried out only once, at the end of the iterative estimation procedure, computation time is not significantly impacted.

Figure 8:
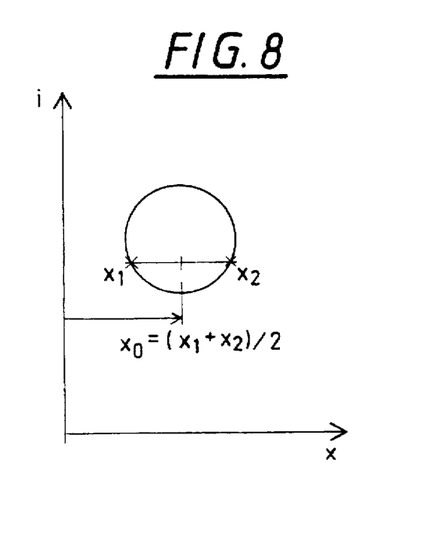
FIGS. 8 and 9 show, in pictorial form, how an embodiment of the present invention is used to find the position of the pupil center.
Figure 9:
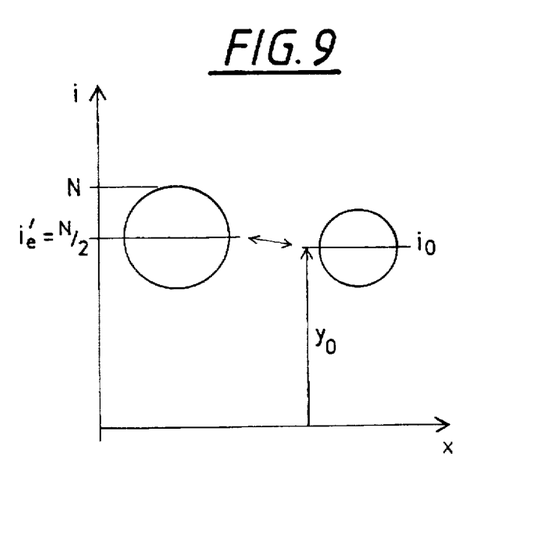

Having described above how to determine the area of the pupil in accordance with the present invention, we now turn to a description of how to determine the position of the center of the pupil with reference to FIGS. 8 and 9. Referring to FIG. 8, the horizontal coordinate of the pupil center ($x_o$) is found from the midpoint of any pupil chord, or preferably from the average of the midpoints of several chords. Thus, as shown in FIG. 8, $x_o=(x_1+x_2)/2$. As one can readily appreciate, the determination of the midpoint of a pupil chord or the average of the midpoints of several chords may be performed in accordance with a number of methods which are well known to those of ordinary skill in the art.

The vertical coordinate of the pupil center ($y_o$) is found as follows. As described above, the iteration method to determine the pupil area can be terminated whenever $i'_e > N/2$, i.e., whenever the center of the reference pupil is crossed. Then, referring to FIG. 9, in accordance with the present invention, the value of i corresponding to $i'_e$ is taken to be equal to the vertical half-height of the pupil being measured. Then, this half-height is added to the y-coordinate of the lower pupil edge (the y-coordinate of the first detected chord of the pupil) to give the vertical coordinate of the pupil center.

Figure 10:
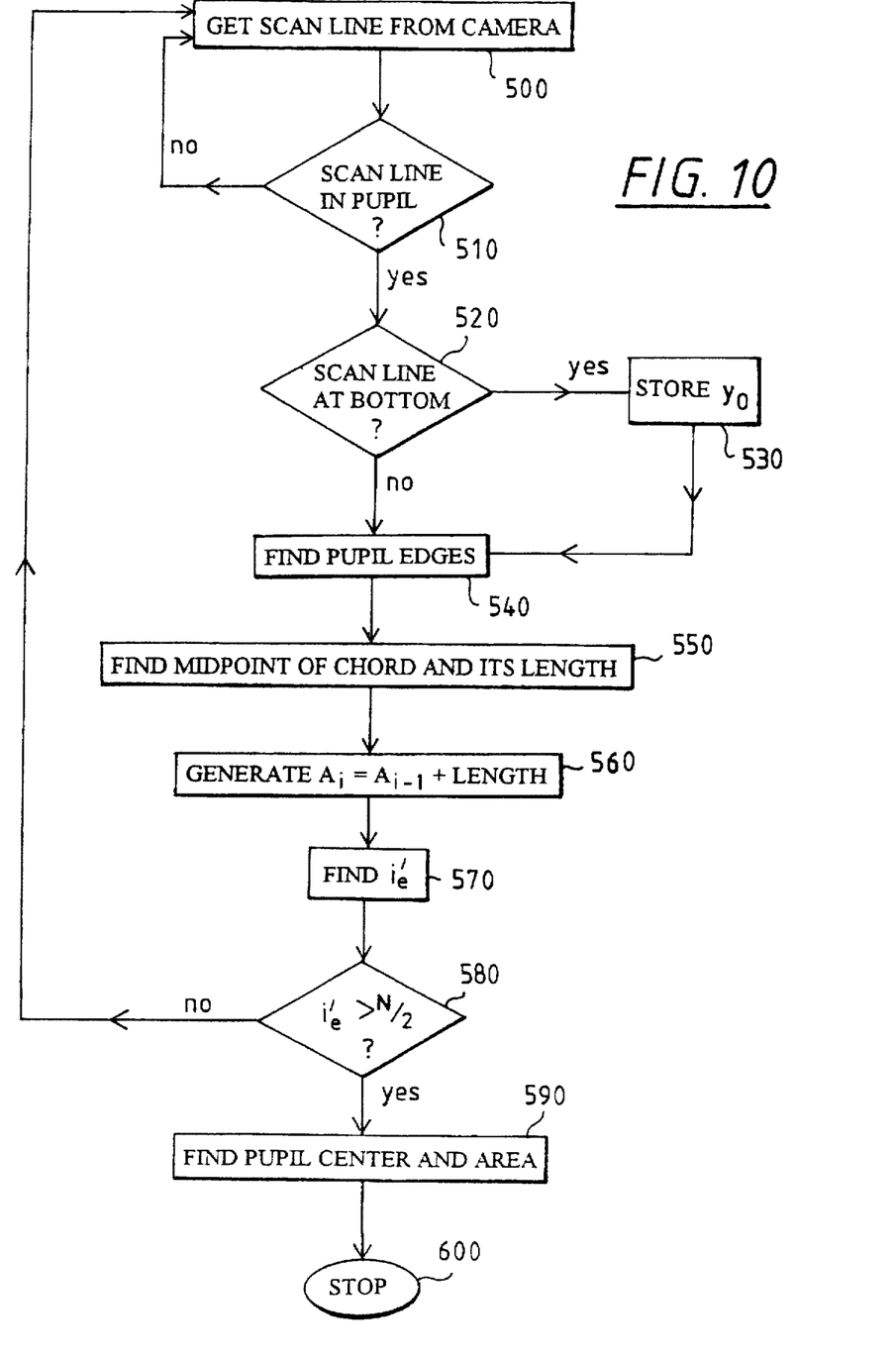
FIGS. 10 and 11 show flowcharts of the inventive method from a point at which horizontal scan line information is input to a controller for a bottom-to-top scan and for a top-to-bottom scan, respectively.
Figure 11:
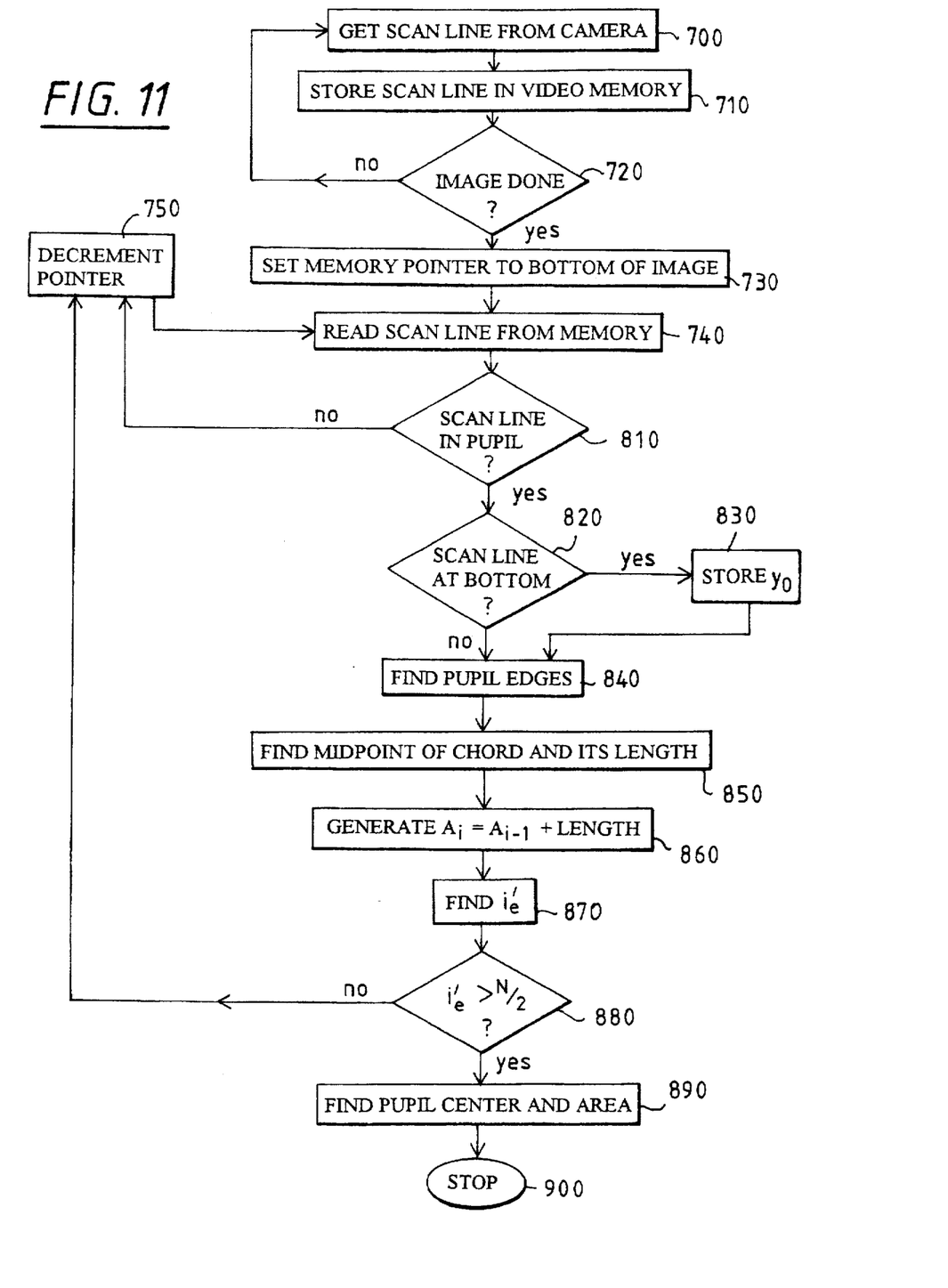

FIGS. 10 and 11 show flowcharts of the inventive method from a point at which horizontal scan line information is input to controller 30 for a bottom-to-top scan and for a top-to-bottom scan, respectively. As shown in FIG. 10, at box 500, a horizontal scan line is received by controller 30 and control is transferred to box 510.

At box 510, if the scan line is in the pupil, control is transferred to box 520, otherwise, control is transferred to box 500.

At box 520, if this horizontal scan line is the first scan line for the pupil, control is transferred to box 530, otherwise, control is transferred to box 540.

At box 530, the y-coordinate is stored as the y-coordinate of the lower pupil edge and control is transferred to box 540.

At box 540, the left and right boundaries of the pupil chord are determined in accordance with methods that are well known in the art and control is transferred to box 550.

At box 550, the midpoint of the chord and the sum of the pixels in the chord are determined and control is transferred to box 560.

At box 560, the sum of the pixels in the chord is added to the previous partial area to determine the partial area for this horizontal scan line and control is transferred to box 570.

At box 570, an estimate of the index for the reference pupil data $i'_e$ is calculated in accordance with eqns. (2) and (3) and control is transferred to box 580.

At box 580, if $i'_e > N/2$, control is transferred to box 590, otherwise, control is transferred to box 500 to wait for the next scan line.

At box 590, the horizontal line index is added to the y-coordinate of the lower pupil edge to provide $y_o$ (the vertical coordinate of the pupil center); the values of the midpoints of the chords are averaged to provide $x_o$ (the horizontal coordinate of the pupil center); and $R_{corr}$ is determined in accordance with eqns. (5) and (6). Lastly, to determine the area of the test pupil, $R_{corr}$ is multiplied by the area of the reference pupil, which area is the partial area of the last chord in the reference pupil.

As shown in FIG. 11, at box 700, a horizontal scan line is received by controller 30 and control is transferred to box 710.

At box 710, the scan line is stored, for example, in a video memory, and control is transferred to box 720.

At box 720, if this is the last horizontal scan line in the 2D image, control is transferred to box 730, otherwise, control is transferred to box 700 to wait to receive the next horizontal scan line.

At box 730, a memory pointer is set to the bottom of the image and control is transferred to box 740.

At box 740, a scan line is retrieved from memory and control is transferred to box 810.

At box 810, if the scan line is in the pupil, control is transferred to box 820, otherwise, control is transferred to box 750.

At box 750, the pointer is decremented and control is transferred to box 740.

At box 820, if this horizontal scan line is the first scan line for the pupil, control is transferred to box 830, otherwise, control is transferred to box 840.

At box 830, the y-coordinate is stored as the y-coordinate of the lower pupil edge and control is transferred to box 840.

At box 840, the left and right boundaries of the pupil chord are determined in accordance with methods that are well known in the art and control is transferred to box 850.

At box 850, the midpoint of the chord and the sum of the pixels in the chord are determined and control is transferred to box 860.

At box 860, the sum of the pixels in the chord is added to the previous partial area to determine the partial area for this horizontal scan line and control is transferred to box 870.

At box 870, an estimate of the index for the reference pupil data $i'_e$ is calculated in accordance with eqns. (2) and (3) and control is transferred to box 880.

At box 880, if $i'_e \geq N/2$, control is transferred to box 890, otherwise, control is transferred to box 750.

At box 890, the horizontal line index is added to the y-coordinate of the lower pupil edge to provide $y_o$ (the vertical coordinate of the pupil center); the values of the midpoints of the chords are averaged to provide $x_o$ (the horizontal coordinate of the pupil center; and $R_{corr}$ is determined in accordance with eqns. (5) and (6). Lastly, to determine the area of the test pupil, $R_{corr}$ is multiplied by the area of the reference pupil, which area is the partial area of the last chord in the reference pupil.

As was described above, the partial area as a function of horizontal scan line index i can be determined from a patient's full-eye scan using a suitably modified version of the above described method, which modification can readily be performed by one of ordinary skill in the art.

The information provided as output from the inventive method and apparatus may be used in several ways. The information may be used in apparatus used to track pupillary response. For such an apparatus, the apparatus shown in FIG. 1 would further include a source of radiation that is visible, for example, to the human eye. Preferably such a source would be operated under the control of controller 30 for automatic operation; although this is not required. Then, in accordance with the present invention, such an apparatus would be used to collect reference data from the patient as was previously described above. Then, the visible light source would be activated and a series of determinations of the area of the pupil would be made as a function of time. These determinations can be plotted, for example, on a display device such as a CRT screen and/or a paper chart output or a printer output to indicate the pupillary response. The velocity of the pupillary response can similarly be determined as the rate of change of pupil area as a function of time. Like information can similarly be used to correlate pupil size with the effects of drugs such as anesthesia.

The information provided as output from the inventive method and apparatus may also be used in apparatus to track gaze direction. As is known in the art, many methods of tracking gaze direction require knowledge of the position of the center of the pupil. As such, the apparatus of FIG. 1 would be utilized as part of apparatus shown, for example, in U.S. Pat. Nos. 5,491,757 and 5,220,361 to determine the center of the pupil. The further information required to determine the gaze direction such as, for example, the detection of a corneal reflex would be obtained in accordance with methods and apparatus disclosed in the above-referenced patents and these pieces of information would be combined in a manner which is well known to those of ordinary skill in the art to determine the gaze direction. Further, by continuous measurement, the gaze direction may be tracked. This is useful for instruments such as visual field analyzers which require a patient to gaze in a predetermined direction and where a need exists to detect changes in gaze direction to monitor whether the data being collected is valid.

Lastly, although the present invention has been described in terms of performing horizontal scans, those of ordinary skill in the art will readily appreciate that vertical scans can also be analyzed directly using the present invention. Further, in one embodiment, the data from vertical scans can be converted to horizontal scan data by appropriate transformation. It is noted that vertical scan information may be useful when the present invention is utilized with pupils from species other than humans.

Those skilled in the art will recognize that the foregoing description has been presented for the sake of illustration and description only. As such, it is not intended to be exhaustive or to limit the invention to the precise form disclosed.

What is claimed is:

1. A method for determining a size of an eye's pupil which comprises the steps of:

storing reference partial areas for a reference pupil that are associated with scan lines of a two-dimensional image of the eye;

analyzing one or more scan lines comprised of pixels from another two-dimensional image of the eye as follows:

determining which of the pixels in an analyzed scan line are in the pupil;

determining a sum of such pixels for the analyzed scan line;

determining a partial area associated with the analyzed scan line by adding the sum to the partial area for previously analyzed scan lines; and estimating the size of the pupil from the partial areas determined from the another two dimensional image and the partial areas for the reference pupil.

2. The method of claim 1 which further comprises obtaining the two-dimensional image by scanning the eye from the bottom to the top.

3. The method of claim 1 wherein the step of estimating the size comprises the steps of:

determining an estimate of a ratio of an area of the pupil and an area of the reference pupil.

4. The method of claim 3 wherein the step of determining an estimate of the ratio comprises the steps of:

determining the estimate of the ratio as a ratio of the partial area of the pupil for the analyzed scan line and a partial area for a corresponding scan line of the reference pupil.

5. The method of claim 4 wherein the step of determining the estimate as a ratio comprises the steps of:

determining an estimate of the corresponding scan line from the estimate of the ratio for the previously analyzed scan line.

6. The method of claim 5 wherein the step of estimating the ratio includes the step of identifying the ratio whenever the estimate of the corresponding scan line equals or exceeds a predetermined fraction of a total number of scan lines in the reference pupil.

7. The method of claim 6 which further comprises correcting the identified estimate of the ratio by an estimated amount which depends on the estimated ratio.

8. The method of claim 7 wherein the step of analyzing further comprises the steps of multiplying the corrected estimated value of the ratio by an area of the reference pupil.

9. A method for determining a position of the center of an eye's pupil which comprises the steps of:

storing reference partial areas for a reference pupil that are associated with scan lines of a two-dimensional image of the eye;

analyzing one or more scan lines comprised of pixels from another two-dimensional image of the eye as follows:

determining which of the pixels in the analyzed scan line are in the pupil and determining a center of gravity for such pixels as one coordinate of the center of the pupil;

determining a sum of such pixels for the analyzed scan line;

determining a partial area associated with the analyzed scan line by adding the sum to the partial area for previously analyzed scan lines;

determining a ratio of the partial area of the pupil and a partial area for an estimate of a corresponding scan line of the reference pupil, wherein the estimate of the corresponding scan line is determined from an estimate of the ratio for the previously analyzed scan line;

identifying a second coordinate of the center of the pupil whenever the estimate of the corresponding scan line equals or exceeds a half of the total number of scan lines in the reference pupil.

10. Apparatus for determining a size of an eye's pupil which comprises the steps of:

a video camera system for obtaining two-dimensional images of the eye;

a processor, responsive to the two-dimensional images, which stores reference partial areas for a reference pupil that are associated with scan lines of the two-dimensional image;

the processor, responsive to a further two-dimensional image of the eye, which analyzes one or more scan lines comprised of pixels from the further two-dimensional image of the eye, which processor comprises:

means for determining which of the pixels in an analyzed scan line are in the pupil;

means for determining a sum of such pixels for the analyzed scan line;

means for determining a partial area associated with the analyzed scan line by adding the sum to the partial area for previously analyzed scan lines; and means for estimating the size of the pupil from the partial area determined from the another two dimensional image and the partial areas for the reference pupil.

* * * * *